(12) United States Patent
Koyama et al.

(10) Patent No.: US 8,047,381 B2
(45) Date of Patent: Nov. 1, 2011

(54) GRAIN CLASSIFYING DEVICE AND ADHESIVE CONTAINING GRAINS CLASSIFIED BY THE DEVICE

(75) Inventors: Keiji Koyama, Osaka (JP); Tetsuya Kuwabara, Osaka (JP); Masaru Haga, Osaka (JP); Hideki Kashihara, Osaka (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 0 days.

(21) Appl. No.: 12/817,666

(22) Filed: Jun. 17, 2010

(65) Prior Publication Data

US 2010/0252781 A1  Oct. 7, 2010

Related U.S. Application Data

(62) Division of application No. 11/664,273, filed as application No. PCT/JP2006/318880 on Sep. 22, 2006.

(30) Foreign Application Priority Data

Sep. 26, 2005  (JP) ................................. 2005-278506

(51) Int. Cl.
*B07C 5/02*  (2006.01)

(52) U.S. Cl. ........ 209/539; 209/544; 209/586; 209/906; 252/500

(58) Field of Classification Search .................. 252/200, 252/500; 209/539, 544, 586, 639, 644, 906, 209/908

See application file for complete search history.

(56) References Cited

U.S. PATENT DOCUMENTS

| 3,790,760 A | 2/1974 | Stiller |
| 3,941,479 A | 3/1976 | Whitehead |
| 4,057,146 A | 11/1977 | Castaneda et al. |
| 4,318,480 A | 3/1982 | Lombardo |
| 4,361,400 A | 11/1982 | Gray et al. |
| 4,781,671 A | 11/1988 | Pober et al. |
| 5,314,071 A | 5/1994 | Christian et al. |
| 5,862,919 A | 1/1999 | Eason |

(Continued)

FOREIGN PATENT DOCUMENTS

JP   64-075054   3/1989

(Continued)

OTHER PUBLICATIONS

International Preliminary Report on Patentability and Written Opinion of the International Searching Authority, issued in corresponding International Patent Application No. PCT/JP2006/318880, dated Apr. 3, 2008.

(Continued)

*Primary Examiner* — Joseph C Rodriguez
(74) *Attorney, Agent, or Firm* — McDermott Will & Emery LLP

(57) ABSTRACT

A grain classifying device for accurately classifying the grains of uniform length, and an adhesive containing grains classified by the device and capable of connecting electrodes under a low pressure and being applicable to electrodes arranged in fine pitches. The grain classifying device (1) includes a dispersing means (2) for dispersing a plurality of grains (P). A grain orienting means (3) orients each of the dispersed grains in a transfer direction (X) of the grains (P) while spacing the grains apart from one another in the transfer direction (X) of the grains. A grain length measuring means (4) measures the length of each of the grains (P) oriented in the transfer direction (X). A grain separation means (5) separates the grains (P) having a predetermined length based on data related to the lengths of the measured grains (P).

1 Claim, 6 Drawing Sheets

U.S. PATENT DOCUMENTS

| | | | |
|---|---|---|---|
| 5,868,255 | A | 2/1999 | McGaa |
| 6,040,544 | A | 3/2000 | Schantz et al. |
| 6,059,117 | A | 5/2000 | Novak et al. |
| 6,211,956 | B1 | 4/2001 | Nicoli |
| 6,254,787 | B1 | 7/2001 | Kimura et al. |
| 6,265,683 | B1 | 7/2001 | Flottmann et al. |
| 6,482,652 | B2 | 11/2002 | Furlong et al. |
| 6,537,385 | B2 | 3/2003 | Okayama et al. |
| 7,572,375 | B2 | 8/2009 | Takagi et al. |
| 7,691,636 | B2 | 4/2010 | Frazier et al. |

FOREIGN PATENT DOCUMENTS

| | | |
|---|---|---|
| JP | 6-41876 | 6/1994 |
| JP | 09-229634 | 9/1997 |
| JP | 10-314680 | 12/1998 |
| JP | 2001-033214 | 2/2001 |
| JP | 2003187885 A * | 7/2003 |
| JP | 2003-286457 | 10/2003 |
| JP | 2005146043 A * | 6/2005 |
| JP | 2005-251584 | 9/2005 |

OTHER PUBLICATIONS

United States Office Action issued in U.S. Appl. No. 11/664,273 dated Jan. 19, 2011.

United States Notice of Allowance, issued in U.S. Appl. No. 11/664,273, dated Jul. 12, 2011.

* cited by examiner

GRAIN CLASSIFYING DEVICE AND ADHESIVE CONTAINING GRAINS CLASSIFIED BY THE DEVICE

RELATED APPLICATIONS

This application is a Divisional of U.S. patent application Ser. No. 11/664,273, filed on Mar. 30, 2007, which is a U.S. National Phase under 35 U.S.C. §371 of International Application No. PCT/JP2006/318880, filed on Sep. 22, 2006, which claims priority from Japanese Application No. 2005-278506 filed Sep. 26, 2005, the entire contents of each of which are hereby incorporated by reference.

FIELD OF THE INVENTION

The present invention relates to a grain classifying device for accurately classifying grains, and an adhesive containing grains separated by the device.

BACKGROUND OF THE INVENTION

In recent trends for electronic equipment having smaller sizes and greater functionality, connection terminals for components are becoming more miniaturized. Thus, in the field of electronic applications, various types of circuit connection adhesives are often used to facilitate the connection of such terminals. For example, to connect an electrode of an electronic component, such as an IC chip, with an electrode of a circuit substrate, such as glass substrate, a method for connecting the electrodes formed on the electronic component and the circuit substrate with a conductive adhesive containing conductive fine grains is employed.

The conductive adhesive is an adhesive in the form of film or paste in which conductive fine grains are dispersed in an insulative resin composition such as epoxy resin. The conductive adhesive is applied between the connection subjects, heated, and pressurized to adhere the connection subjects. More specifically, the heating pressurization moves the resin in the adhesive so as to seal, for example, gaps between a projection electrode (or bump) formed on the surface of an electronic component and a wiring electrode such as ITO electrode formed on the surface of a circuit substrate. At the same time, some of the conductive fine grains bite into the opposing projection electrode and wiring electrode to establish electric connection.

Due to recent trends for higher integration, the pitch between adjacent electrodes is becoming increasingly narrower, and pitches are becoming finer. Thus, electrode connection conductive adhesive must use conductive fine grains having small grain diameters.

Accordingly, various types of classifying devices for classifying conductive fine grains have been disclosed. More specifically, there has been a proposal for a current type classifying device including a disperser for dispersing fed dry grains into a primary grain state and continuously discharging dispersed fluid, and a cyclone tower connected immediately after a discharge port of the dispersed powder arranged in the disperser (see e.g., patent document 1).

The cyclone tower includes a spiral type powder inlet portion having a barrel, which serves as a main body for the cyclone tower and has a generally vertical tubular shape, and a powder guide inner wall surface arranged on the upper surrounding of the barrel. The disperser blows dispersed powder in the horizontal direction into the powder inlet portion, which gradually guides the dispersed powder radially inwardly with the power guide inner wall surface so as to produce a winding flow proceeding toward the inner wall surface of the lower barrel. Further, the cyclone tower includes a primary air outlet tube used to discharge grains. The primary air outlet tube extends downward over a certain length along the radially central position of the barrel from the ceiling of the cyclone tower and has an open lower end. The cyclone tower also includes a storage tank, which is connected to the lower open end of the cyclone tower, to store coarse grains that fall from the open lower end. During classification, a blower connected to the primary air outlet tube by way of a filter for collecting fine grains is operated under a predetermined flow rate to generate a current that circulates from the inside of the barrel of the cyclone tower and through the primary air outlet tube. Then, in this state, a power feeder continuously feeds powder to the disperser, and dispersed grains enter the powder inlet portion of the cyclone tower at a predetermined flow rate. The current containing the grains entering the powder inlet portion forms a winding flow along the spiral inner wall surface of the powder inlet portion. The winding flow descends as it is guided in a manner winding along the entire circumference of the inner wall of the barrel. Air is discharged out of the barrel through the primary air outlet tube. The current winding along the inner wall of the barrel generates a rising current at the central portion of the barrel while descending in the conical barrel. Therefore, in the grains contained in the current that descends while winding in the barrel of the cyclone tower, the grains having a large diameter and a relatively large weight settles downward and falls into the coarse powder storage tank connected to the lower open end of the barrel in accordance with the balance between the transfer action received from the current and the centrifugal force resulting from the mass of the grains. The grains having a small diameter and a relatively small weight pass through a fine grain transfer tube via the primary air outlet tube and are transferred to a filter by the action of the transferring force of the current discharged out of the primary air outlet tube. With this structure, grains having a diameter of 10 µm or smaller are sufficiently classified for industrial use.

Patent document 1: Japanese Patent Publication No. 2580193

SUMMARY OF THE INVENTION

Generally, the conductive fine grains mentioned above are manufactured through various methods such as a gas phase method or a liquid phase method, and have a grain length distribution in the range of 1 µm to 30 µm. However, due to the finer pitches of electrodes, the conductive adhesive for electrode connection must contain conductive fine grains having the same grain length (e.g., needle-shaped conductive fine grains having substantially the same length) in addition to having a small grain diameter.

In the conventional current type classifying device, the fine grains having short grain lengths tend to easily stick to coarse grains having long grain length when classifying needle-shaped conductive fine grains. Thus, accurate grain classification based on grain length is difficult, and the separation of only grains having the desired length is not possible. Therefore, referring to FIG. 7, when using a conductive adhesive 71 containing needle-shaped conductive fine grains 70 classified by the current type conventional classifying device to connect a projection electrodes 73 of an electronic component 72 to wiring electrodes 75 of a circuit substrate 74, the conductive fine grains 70 do not have uniform grain lengths. Thus, when connecting electrodes with the conductive adhesive 71 by performing heating and pressurizing process, it becomes difficult to connect electrodes with a low pressure (e.g., 2 to 5 MPa). Thus, electrodes cannot be connected with a low pressure. Further, an increase in pressure to connect the electrodes would affect the orientation of the conductive fine grains 70. This may lead to a connection failure or short-circuiting of the electrodes. As a result, it would be difficult to connect fine pitch electrodes.

It is an object of the present invention to provide a grain classifying device for accurately classifying grains having the same length and an adhesive containing grains classified by the device capable enabling electrode connection under a low pressure and being applicable to fine pitch electrodes.

To achieve the above object, a first aspect of the present invention provides a grain classifying device. The grain classifying device includes a dispersing means for dispersing a plurality of grains. A grain orienting means orients each of the dispersed grains in a predetermined direction while spacing the grains apart from one another in the predetermined direction. A grain length measuring means measures the length of each of the grains oriented in the predetermined direction. A grain separation means separates the grains having a predetermined length from the dispersed grains based on data related to the lengths of the measured grains.

With such a structure, the plurality of grains are dispersed, and the grains are oriented in the desired direction in a state spaced apart from one another. This prevents fine grains having short grain lengths from sticking to coarse grains having long grain lengths. Further, the length of each grain is measured, and only grains having the desired length are separated. As a result, the grains are accurately classified.

In the grain classifying device, the dispersing means preferably performs dispersion with ultrasonic waves using ultrasonic wave. With such a structure, conglomerates of grains, which are the separation subject, are dispersed into primary grains that are not conglomerates or into a state close to primary grains.

In the grain classifying device, the grain orienting means preferably includes a flow passage for passage of the grains, and the grains are oriented when passing through the flow passage. Thus, the dispersed grains are each oriented in a state spaced apart from one another with a simple structure.

In the grain classifying device, the grain length measuring means preferably includes an illumination unit for emitting light that illuminates the grains, an image capturing unit for capturing an image of a reflected light reflected by the grains, and a computation processor for computing the lengths of the grains based on the image captured by the image capturing unit. Thus, the length of each grain is accurately measured with a simple structure.

In the grain classifying device, the grain separation means preferably includes a separator for separating the grains having the predetermined length from the dispersed grains and a control means for controlling the separator based on data related to the lengths of the measured grains. In this case, the control means determines whether or not the lengths of the measured grains is the predetermined length and controls the separator so that the grains having the predetermined length are separated from the dispersed grains based on the determination result. Thus, only grains having the desired length are separated with a simple structure.

It is preferred that the grain classifying device further includes a reprocessing means for supplying grains other than the grains that have the predetermined length and are separated by the grain separation means from the grain separation means to the dispersion means. With such a structure, the grains that are not separated by the grain separation means are reprocessed by the grain classifying device. The enables continuous and efficient grain classification.

A second aspect of the present invention provides an anisotropic conductive adhesive. The anisotropic conductive adhesive contains grains having a predetermined length classified by the above grain classifying device. The grains are conductive fine grains that are needle-shaped.

With such a structure, the conductive fine grains contained in the anisotropic conductive adhesive have substantially the same length and a uniform grain length.

Thus, when connecting projection electrodes of an electronic component to wiring electrodes of a circuit substrate with the anisotropic conductive adhesive, the conductive fine grains bite into the projection electrodes and wiring electrodes under a low pressure (e.g., 2 to 5 MPa). As a result, the electrodes are connected with a low pressure.

The orientation of the conductive fine grains is not affected since the pressure for connecting the electrodes is low. Therefore, electrodes are connected at a fine pitch.

Further, the conductive fine grains are needle-shaped, and the pressure for connecting electrodes is low. Thus, electronic components, such as semiconductor element, can be mounted on a circuit substrate by the anisotropic conductive adhesive containing the conductive fine grains without damaging the electronic components.

The grain classifying device of the present invention enables separation of only the grains having the desired length and enables accurate classification of the grains. Furthermore, the anisotropic conductive adhesive of the present invention enables the connection of electrodes with a low pressure and enables application to electrodes of fine pitches.

DETAILED DESCRIPTION OF THE PREFERRED EMBODIMENTS

Figure 1:
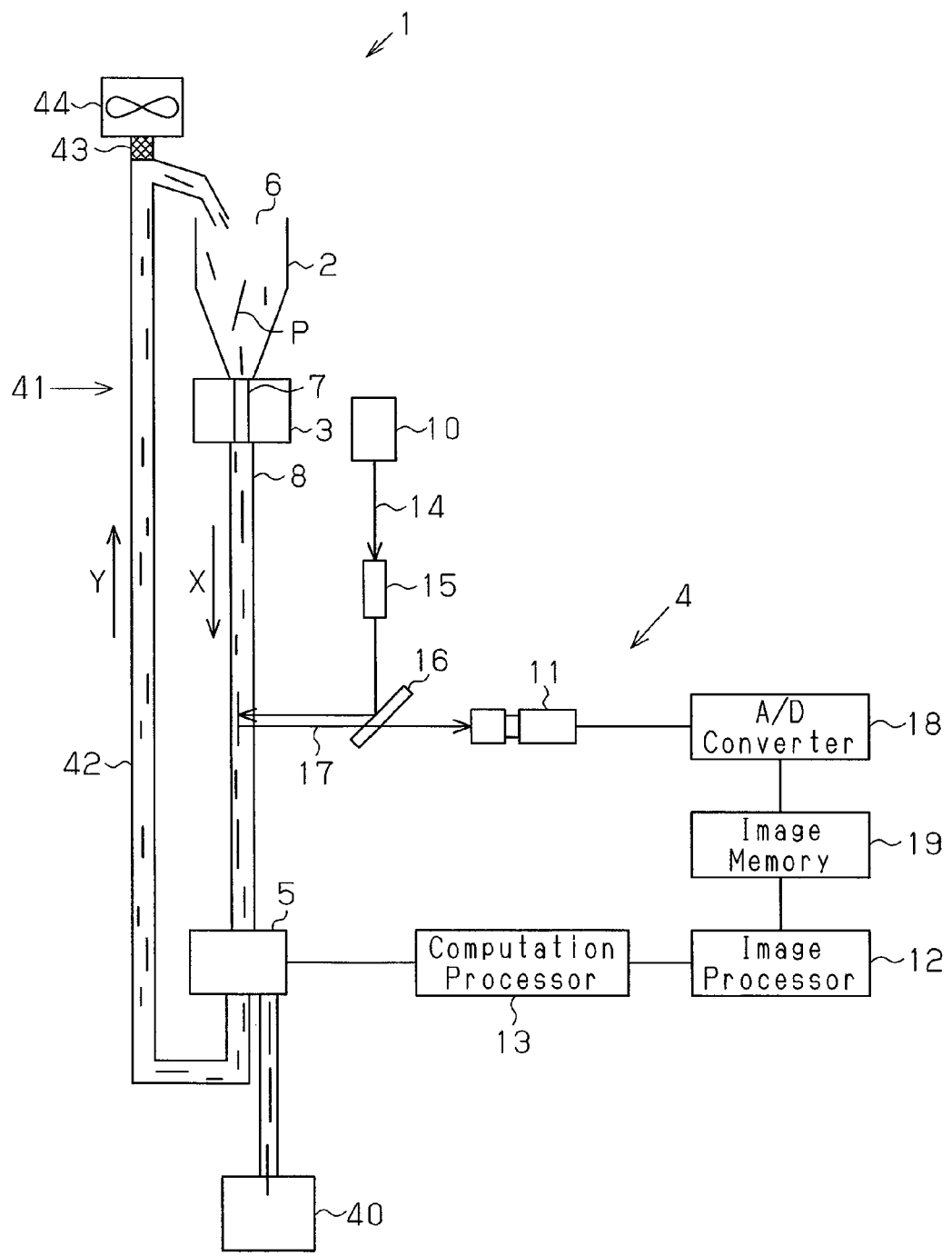
FIG. 1 is a schematic diagram showing the entire structure of a grain classifying device according to a preferred embodiment of the present invention.

One embodiment of the present invention will now be described with reference to the drawings. FIG. 1 is a schematic diagram showing the entire structure of a grain classifying device 1 according to one embodiment of the present invention. The grain classifying device 1 separates the grains based on the grain length. As shown in FIG. 1, the grain classifying device 1 includes a dispersing means 2 for dispersing the grains, which are the separation subject, and a grain orienting means 3 for orienting the grains dispersed by the dispersing means 2 in a predetermined direction. The grain classifying device 1 further includes a grain length measuring means 4, which measures the length of each grain oriented in the predetermined direction, and a grain separation means 5, which separates grains having a predetermined length based on data of the measured grain length.

Grains classified by the grain classifying device 1 of the present invention may be conductive fine grains contained in an anisotropic conductive adhesive used to connect, for example, an electrode formed on a semiconductor element such as IC chip and an electrode formed on a circuit substrate. The conductive fine grains may be needle-shaped and have a large so-called aspect ratio. Here, the aspect ratio refers to the ratio between the minor axis of the conductive fine grain (cross-sectional length of a conductive fine grain) and the major axis (length of conductive fine grain).

When classifying the grains with the grain classifying device 1, grains P serving as the classified subject are fed into the dispersing means 2 from a feeding portion 6 defined in the dispersing means 2, as shown in FIG. 1. The dispersing means 2 may be of any type as long as conglomerates of the grains P serving as the classified subject are dispersed into primary grains that are not in conglomerates or into a state close to the primary grains. For example, the dispersing means 2 may perform dispersion with ultrasonic wave (using an ultrasonic wave dispersion oscillator).

Higher dispersion effects may be obtained by adding conglomerates of the grains P to a dispersion solvent and emitting ultrasonic waves to the dispersion solvent to disperse the grains P in the dispersion solvent. An alcohol, such as methanol, ethanol, butanol, or propanol, and an organic solvent, such as methyl ethyl ketone, may be used as the dispersion solvent. The dispersion solvent may be selected and used in accordance with the type of grains P that are dispersed. Further, one type of a dispersion solvent may be used alone or a plural types of dispersion solvents may be mixed and used.

The grains P dispersed by the dispersing means 2 move towards the grain orienting means 3. The grain orienting means 3 spaces apart the grains P dispersed by the dispersing means 2 in a predetermined direction (i.e., grain transfer direction, which is the direction of arrow X in FIG. 1) while orienting each grain in the transfer direction X. The grain orienting means 3 preferably includes a flow passage 7, through which the dispersed grains P pass. The flow passage 7 has a diameter that is slightly larger than the minor axis of the grain P (about five times the diameter of the grain P). The grain orienting means 3 orients each grain P dispersed by the dispersing means 2 in the transfer direction X of the grain P when passing through the flow passage 7. Thus, with a simple structure, the dispersed grain P is orientated in the transfer direction X while being spaced apart from one another in the transfer direction X.

The grains P orientated in the transfer direction X by the grain orienting means 3 pass through a transfer portion 8 to be transferred to the grain length measuring means 4 while being maintained the oriented state. The grain length measuring means 4 includes an illumination unit 10 for emitting light that illuminates the grains P, an image capturing unit 11 for capturing the image of reflection light reflected by the grains P, and a computation processor 13 for computing the length of a grain P based on the image captured by the image capturing unit 11.

A collimator lens 15 arranged along the optical path of light 14 emitted from a light source, or the illumination unit 10, suppresses diffusion of the light 14 and forms a generally parallel light beam. Furthermore, the light 14 is guided towards a half mirror 16 by the collimator lens 15 and emitted toward the grains P by the half mirror 16. The image of the reflected light 17 reflected by the grains P is captured by a CCD camera sensor, or the image capturing unit 11, which has a light receiving surface facing a direction orthogonal to the transfer direction X of the grains P.

An original image captured by the CCD camera sensor is converted from an analog signal to a digital signal by an A/D converter 18 and stored in an image memory 19. The image data stored in the image memory 19 is provided to an image processor 12. The image processor 12 performs image processing such as expansion and contraction processes or binary processing on the original image captured by the image capturing unit 11 to generate a processed image. This image processing clarifies the original image captured by the CCD camera sensor and emphasizes the profile of a grain image.

Generally, the expansion process refers to a process for setting a certain pixel to 1 if there is at least one proximal pixel (e.g., adjacent four or eight pixels) set at 1 (e.g., white), and the contraction process refers to a process for setting a certain pixel to 0 if there is at least one proximal pixel set at 0 (e.g., black). In the present embodiment, an expanded image in which foreign matters are eliminated from the original image is generated by performing the expansion process on the original image captured by the CCD camera sensor. The contraction process is then performed on the expanded image to generate an expanded and contracted image clearly showing the profile of a grain P.

Generally, with regard to the brightness of an image, the binary processing processes a pixel having a brightness greater than a predetermined determination threshold value as white and a pixel having low brightness as black. In the present embodiment, the expansion and contraction processes described above are performed on the original image captured by the CCD camera sensor, and the binary processing is performed on the obtained expanded and contracted image to generate a binary image in which the profile of the grain P is clarified. After the expansion and contraction processes and the binary processing are sequentially performed on the original image captured by the CCD camera sensor, the binary processing result may be inverted. That is, using the determination results based on the predetermined threshold value for image brightness, the image processor 12 may be configured to process pixels determined to be white as black pixels and pixels determined to be black as white pixels.

An image processing signal based on the processed image generated by the image processor 12 is provided to the computation processor 13. The computation processor 13 computes the total number of pixels forming each grain P based on the image processing signal to compute the length of each grain P based on the total number of pixels. More specifically, the computation processor 13 computes the length of each grain P by multiplying a predetermined pixel length by the total number of pixels forming each grain P.

If the total number of pixels forming a grain P is twelve, and the length of a pixel is set to 250 nm, the grain length is computed to be 3 µm. Therefore, in the present embodiment, the computation processor 13 is configured to compute the length of each grain P based on the processed image generated by the image processor 12. This enables the length of each grain P to be accurately computed.

Figure 2:
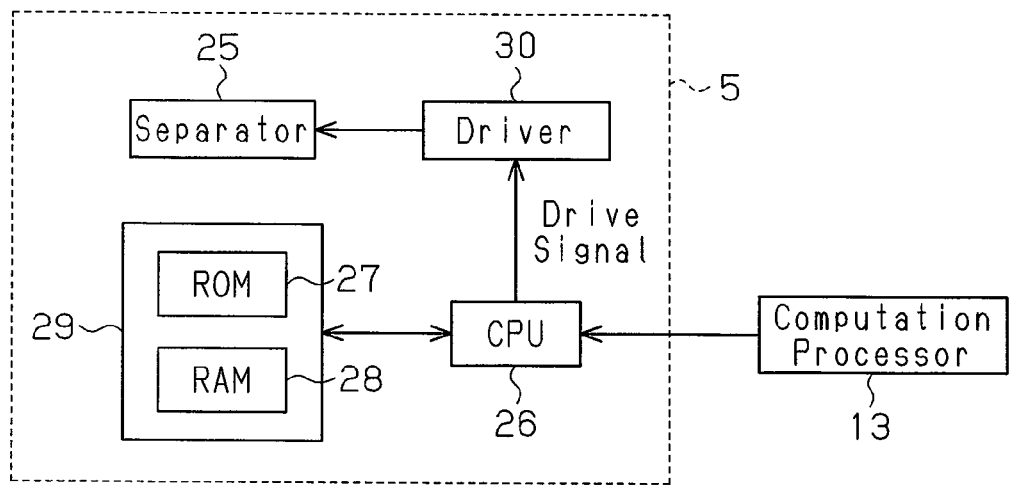
FIG. 2 is a schematic diagram showing the entire structure of a grain separation means in the grain classifying device of FIG. 1.

Furthermore, as shown in FIG. 1, the grain separation means 5 is connected to the computation processor 13, and the data related to the length of each grain P computed by the computation processor 13 is provided to the grain separation means 5. The grain separation means 5 separates the grains P based on the data related to the length of the grains P computed in the above manner. As shown in FIG. 2, the grain separation means 5 includes a separator 25 for separating and collecting the grains P, a CPU 26 serving as a control means for controlling the separator 25, a memory 29 including a ROM 27 and a RAM 28, and a driver 30 for driving the separator 25. A drive pulse signal (hereinafter referred to as the "drive signal") generated by the CPU 26 is provided to the driver 30, and the driver 30 drives the separator 25 based on the drive signal. The memory 29 is connected to the CPU 26, and the CPU 26 controls the separator 25 in accordance with programs stored in the ROM 27.

Further, as shown in FIG. 2, the CPU 26, which is connected to the computation processor 13 and the driver 30, is provided with the data related to the length of the grains P by the computation processor 13. The CPU 26 generates the drive signal based on the input data.

More specifically, the CPU 26 reads from the memory 29 the predetermined grain length stored in the memory 29 and determines whether or not the length of the grains P based on the input data is the predetermined grain length. If the length of the grains P based on the input data is the predetermined grain length, the CPU 26 generates the drive signal to drive the separator 25. The drive signal is then provided to the driver 30, and the driver 30 drives the separator 25. As a result, the grains P having the predetermined length are attracted toward the separator 25 and separated, and the separated grains P are transferred to and collected by the collector 40 shown in FIG. 1. If the length of the grains P based on the input data does not have the predetermined grain length, the CPU 26 does not generate the drive signal. Therefore, the separator 25 is not driven, and the grains P that do not have the predetermined length are transferred to a reprocessing means 41 shown in FIG. 1 without being transferred to the collector 40. As for conglomerates of grains P that were not dispersed into primary grains or a state close to the primary grains by the dispersing means 2, the CPU 26 determines that the grains P do not have the predetermined grain length. The conglomerates of grains P are thus transferred to the reprocessing means 41 without being drawn toward the separator 25. In this manner, in the present embodiment, the CPU 26 is configured to control the separator 25 based on the data related to the length of the grains P computed by the computation processor 13. Accordingly, only grains P having the desired length are separated. Thus, the grains P are accurately separated.

An electromagnet having a metal coil wound around a core made of steel or the like may be used as the separator 25. In this case, when the input data shows that the grains P have the predetermined grain length and the driver 30 drives the separator 25 in response to the drive signal, high frequency current having the predetermined frequency flows to the coil from a high frequency power supply, which is connected to the coil. This generates electromagnetic induction and the core temporarily becomes a magnet. A magnetic field is generated in the transfer portion 8 near the magnet, and grains having the predetermined grain length (e.g., conductive grains that are metal fine grains) are attracted toward the magnet and separated. When the input data shows that the grains P do not have the predetermined grain length, the grains P are transferred to the reprocessing means 41 without being attracted to the electromagnet. Only the grains P having the desired length are separated, and accurate separation of the grains P is performed with a simple structure.

The reprocessing means 41 supplies grains P other than those having the predetermined length and separated by the grain separation means 5 (i.e., grains that are not separated by the grain separation means 5) from the grain separation means 5 to the dispersing means 2. The reprocessing means 41 includes a transfer portion 42 for connecting the dispersing means 2 and the grain separation means 5, a filter 43 connected to the transfer portion 42 to prevent the grains P from being discharged out of the grain classifying device 1, and an intake fan 44 connected to the filter 43 and serving as a suction means for drawing in air and grains through the filter 43.

When the intake fan 44 starts operating, the air in the transfer portion 42 is drawn into the dispersing means 2 via the transfer portion 42. Furthermore, some of the intake air passes the intake fan 44 through the filter 43 and is discharged outside.

The grains P transferred to the reprocessing means 41 without being attracted to the separator 25 are drawn toward the dispersing means 2 through the transfer portion 42 in the direction of arrow Y, which is shown in FIG. 1, by the air suction force of the intake fan 44. The grains P then enter the dispersing means 2. The grains P are reprocessed by the dispersing means 2, the grain orienting means 3, the grain length measuring means 4, and the grain separation means 5. Accordingly, the grains P that are not separated by the grain separation means 5 are continuously and efficiently classified due to the reprocessing performed by the grain classifying device 1.

Figure 3:
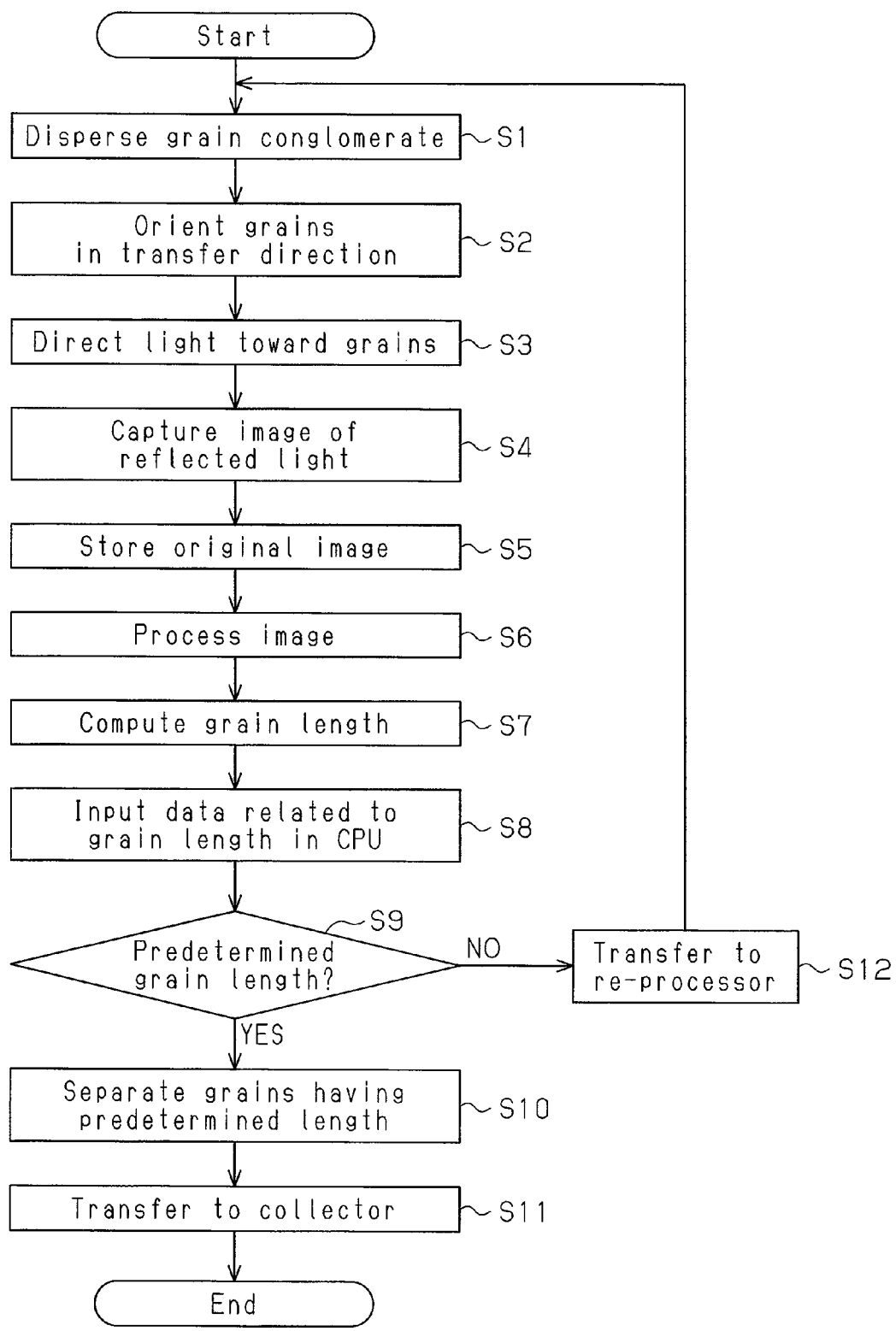
FIG. 3 is a flowchart showing the grain classifying procedures taken by the grain classifying device of FIG. 1.

FIG. 3 is a flowchart showing the grain classifying procedures in the grain classifying device 1 according to one embodiment of the present invention. First, conglomerates of the grains P fed into the dispersing means 2 are dispersed into primary grains that are not in conglomerates or into a state close to the primary grains by the dispersing means 2 (step S1). The grains P dispersed by the dispersing means 2 are then each oriented in the transfer direction X by the grain orienting means 3 (step S2). Light 14 emitted from the light source is directed towards the grains P transferred to the grain length measuring means 4 (step S3), and the image of the reflected light is captured by the CCD camera sensor (step S4). The original image captured by the CCD camera sensor is stored in the image memory 19 (step S5). The image data stored in the image memory 19 is provided to the image processor 12, and image processing is performed on the original image captured by the image capturing unit 11 by the image processor 12 to generate a processed image (step S6). The image processing signal based on the processed image generated by the image processor 12 is provided to the computation processor 13, and the computation processor 13 computes the length of each grain P based on the processed image (step S7). The data related to the length of the grains P computed by the computation processor 13 is provided to the CPU 26 of the grain separation means 5 (step S8). The CPU 26 determines from the input data whether or not the grains P have the predetermined grain length (step S9). If the grains P have the predetermined grain length, the separator 25 is driven, the grains P having the predetermined length are separated by the separator 25 (step S10), and the separated grains P are transferred to the collector 40 (step S11). If the grains P do not have the predetermined grain length, the separator 25 is not driven. Therefore, the grains P that do not have the predetermined length are transferred to the reprocessing means 41 without being transferred to the collector 40 (step S12). The grains P are then drawn into the dispersing means 2 by the reprocessing means 41, and the processes of step S1 to step 9 are performed again.

As described above, the present invention includes the dispersing means 2 for dispersing the grains P, the grain orienting means 3 for orienting each of the dispersed grains P in the transfer direction X in a state in which the grains P are spaced apart in the transfer direction X of the grains P, the grain length measuring means 4 for measuring the length of each oriented grain P, and the grain separation means 5 for separating the grains P having the predetermined length based on the data related to the measured grain P length. Accordingly, the grains P are dispersed, spaced apart, and oriented in the transfer direction X. This avoids fine grains having short lengths from sticking to coarse grains having long grain lengths. Furthermore, the length of each grain P is measured. Thus, only grains P having the desired length are separated. As a result, accurate classification of the grains P is performed.

An adhesive containing grains P having the desired length (i.e., grains having substantially the same length) classified by the grain classifying device 1 in the present embodiment can be manufactured. More specifically, when using conductive fine grains as the grains P that are classified, an anisotropic conductive adhesive containing the conductive fine grains having the desired length classified by the grain classifying device 1 and using a thermosetting resin as the main component is manufactured.

In particular, if the conductive fine grains are needle-shape as described above, each of the conductive fine grains contained in the anisotropic conductive adhesive has substantially the same length, and the grain lengths are uniform. Thus, referring to FIG. 4, when connecting projection electrodes 34 of an electronic component 33 to wiring electrodes 36 of a circuit substrate 35 with an anisotropic conductive adhesive 32 through heating and pressurizing processes, the conductive fine grains 37 bite into the projection electrodes 34 and the wiring electrodes 36 under a low pressure (e.g., 2 to 5 MPa). As a result, the projection electrodes 34 and the wiring electrodes 36 are connected under a low pressure. The orientation of the conductive fine grains 37 is not affected since the pressure for connecting the electrodes is low. As a result, the electrodes are connected in a fine pitch. The electronic components 33 may be mounted on the circuit substrate 35 by the anisotropic conductive adhesive 32 containing the conductive fine grains 37 without damaging the electronic components 33, such as a semiconductor element, since the conductive fine grains 37 are needle-shaped and electrodes are connected with a low pressure.

Figure 4:
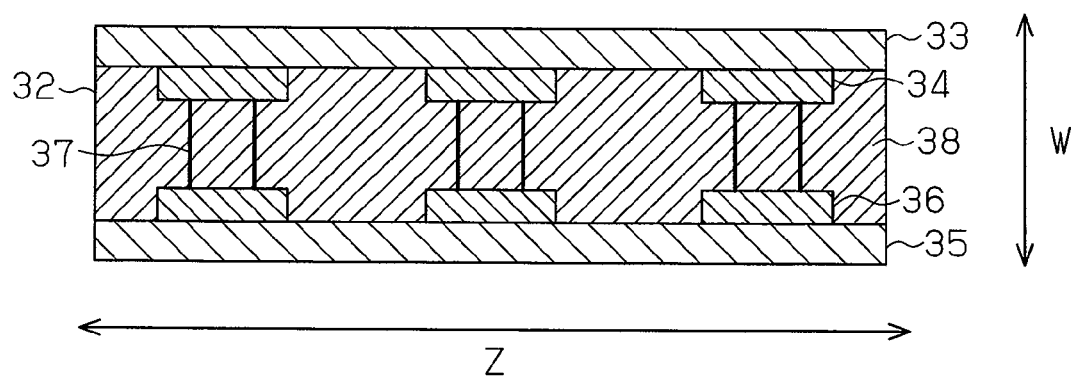
FIG. 4 is a cross-sectional view showing a circuit substrate on which electronic components are connected by an adhesive containing grains classified by the grain classifying device of FIG. 1.

Furthermore, the anisotropic conductive fine grains 37 are preferably oriented in the thicknesswise direction (magnetic field direction, which is the direction shown by arrow W in FIG. 4) by passing through a magnetic field generated in the thicknesswise direction of the anisotropic conductive adhesive 32 when the anisotropic conductive adhesive 32 is manufactured. Such orientation maintains the insulation between adjacent electrodes and prevents short-circuiting due to the high conductive resistance in the planar direction of the anisotropic conductive adhesive 32 (direction orthogonal to the thicknesswise direction W, which is the direction of arrow Z in FIG. 4). Further, a large number of electrodes are simultaneously and independently connected in a conductive manner by the low conductive resistance in the thicknesswise direction W of the anisotropic conductive adhesive 32.

The thermosetting resin 38 used in the anisotropic conductive adhesive 32 includes materials such as epoxy resin, phenol resin, polyurethane resin, unsaturated polyester resin, polyimide resin, and urea resin. Among these materials, epoxy resin may be used for the thermosetting resin 38 to improve the film formation property, heat resistance, and adhesive force of the adhesive.

Further, the anisotropic conductive adhesive 32 containing a latent hardener may also be used. The latent hardener has superior storage stability under low temperatures and subtly produces a hardening reaction under room temperatures. However, the latent hardener rapidly produces a hardening reaction when predetermined temperature conditions are satisfied through heating and the like. Examples of a latent hardener include imidazole series, hydrazide series, amine series such as boron trifluoride-amine complex, amine imide, polyamine, third amine groups, alkyl urea, dicyandiamide series, acid and acid anhydride hardener, basic active hydrogen compound, and modified products of these materials. The listed materials may be used alone or as a mixture of two or more types.

The present invention is not limited to the above embodiment and various modifications are possible.

Figure 5:
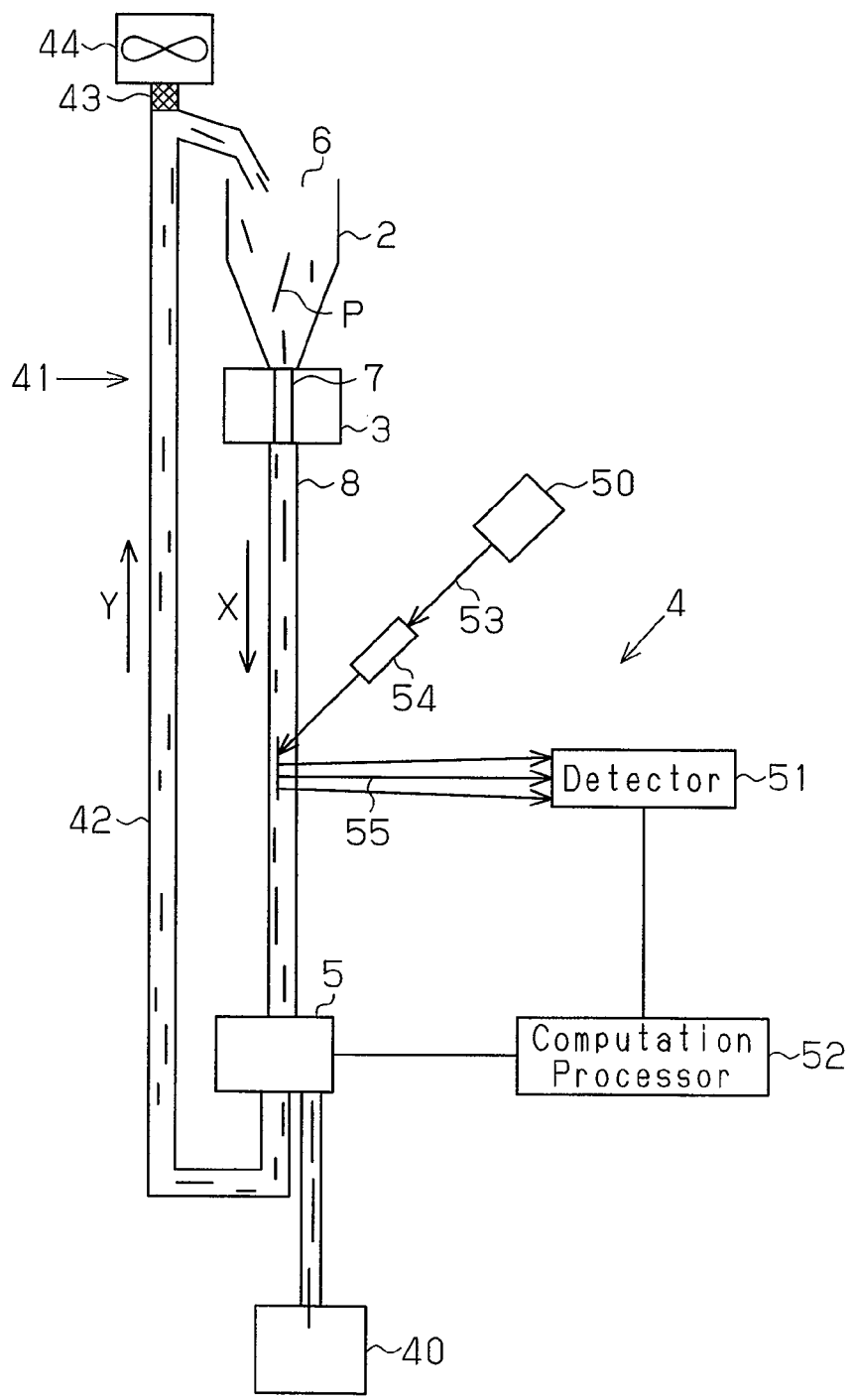
FIG. 5 is a schematic diagram showing the entire structure of another grain classifying device according to the present invention.
Figure 6:
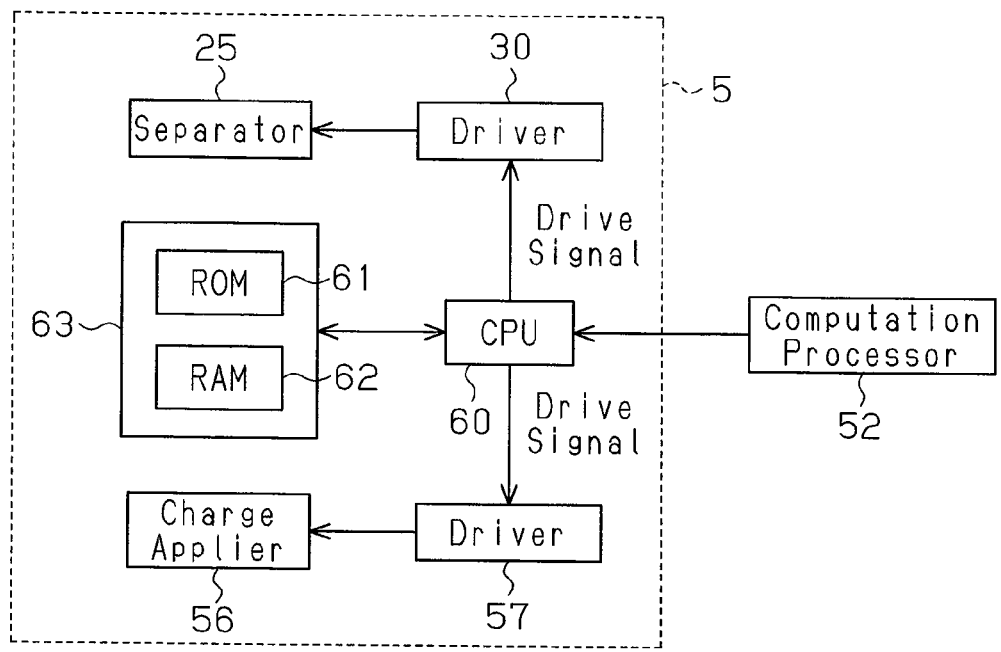
FIG. 6 is a schematic diagram showing the entire structure of a grain separation means in the grain classifying device of FIG. 5.
Figure 7:
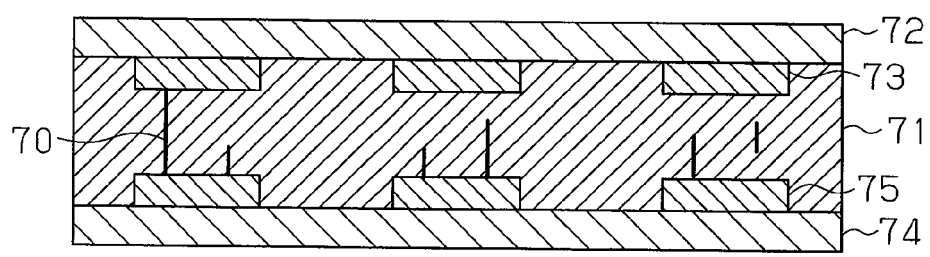
FIG. 7 is a cross-sectional view showing a circuit substrate on which electronic components are connected by an adhesive containing grains classified by a conventional grain classifying device.

For example, in the above embodiment, the dispersing means 2 may disperse each grain P by enclosing a single grain P in a liquid droplet instead of performing dispersion with ultrasonic waves. Further, in the above embodiment, the grain length measuring means 4 captures the image of the reflected light of the light illuminating the grains P and computes the length of the grains P based on the captured image. However, as shown in FIG. 5, the grain length measuring means 4 may direct a laser light to the grains P, detect the scattered light produced by the grains P, and compute the length of the grains P based on the detected scattered light. Further, in the above embodiment, as shown in FIG. 6, the grain separation means 5 may separate the grains P with an electric field using two deflection electrodes instead of the electromagnet in which the metal coil is wound around a coil made of steel or the like.

More specifically, the dispersing means 2 for dispersing each grain P by enclosing the single grain P in the liquid droplet includes a nozzle (not shown) arranged at the lower end of the dispersing means 2 connected to the grain orienting means 3 and including an ejection port and an ultrasonic transducer (not shown) arranged on the upper surface of the nozzle. A liquid (e.g., electrolyte solution such as sodium chloride solution and potassium chloride solution) containing the grain P is fed into the dispersing means 2 from the feeding portion 6, and the liquid containing the grain P is supplied to the nozzle of the dispersing means 2. The ultrasonic transducer applies vertical vibration to the nozzle at a frequency of 25 to 30 kHz and ejects the liquid containing the grain P from the ejection port of the nozzle towards the grain orienting means 3. As a result, the liquid droplet containing one grain P moves towards the grain orienting means 3. Therefore, a conglomerate of grains P, which is the separation subject, is dispersed into primary grains that are not in a conglomerate or into a state close to primary grains.

The liquid droplets containing the grains P oriented in the transfer direction X by the grain orienting means 3 then pass through the transfer portion 8 while maintaining the orientated state of the grains P and are transferred to the grain length measuring means 4 shown in FIG. 5. The grain length measuring means 4 includes a laser light illumination unit 50 for emitting the laser light onto the grains P, a detector 51 for detecting the light scattered by the grains P, and a computation processor 52 for computing the length of each grain P based on the scattered light detected by the detector 51.

The laser light 53 emitted from the light source, or the laser light illumination unit 50, is collected by a convex lens 54, which is arranged on the optical path of the laser light 53, to collimate the laser light 53 that irradiates the grains P. The scattered light 55 reflected by the grains P is detected by the detector 51.

The data based on the detected scattered light 55 is input to the computation processor 52, which computes the length of each grain P. In this case, the scattered light 55 indicates the internal configuration, property, nature and the like of each grain P since it changes in accordance with the modes, such as index of refraction, and size (grain diameter and grain length), of each grain P. The computation processor 52 computes the length of each grain P based on the data of the scattered light 55. The length of each grain P is thus accurately computed.

As shown in FIG. 5, the grain separation means 5 is connected to the computation processor 52, and the data related to the length of each grain P computed by the computation processor 52 is provided to the grain separation means 5. The grain separation means 5 includes a charge applier 56 for applying charges to the liquid droplet containing the grain P having the predetermined grain length, a separator 25 for separating and collecting the grains P having the predetermined grain length, a CPU 60 serving as a control unit for controlling the separator 25 and the charge applier 56, a memory 63 including a ROM 61 and a RAM 62, a driver 30 for driving the separator 25, and a driver 57 for driving the charge applier 56.

Drive signals generated by the CPU 60 are respectively provided to the drivers 30 and 57. The drivers 30 and 57 respectively drive the separator 25 and the charge applier 56 based on the drive signals. The memory 63 is connected to the CPU 60, and the CPU 60 controls the separator 25 and the charge applier 56 in accordance with programs stored in the ROM 61.

The computation processor 52 and the drivers 30 and 57 are connected to the CPU 60. The data related to the length of the grains P computed by the computation processor 52 is provided to the CPU 60 based on the scattered light 55 of the grain P. The CPU 60 generates the drive signals based on the input data.

More specifically, the CPU 60 reads from the memory 63 a predetermined grain length stored in the memory 63 and determines from the input data whether or not the grains P have the predetermined grain length. If grains P have the predetermined grain length, the CPU 60 generates the drive signals to drive a pair of deflection electrodes, which is the separator 25, and the charge applier 56. The drive signals are respectively provided to the drivers 30 and 57. The driver 57 first drives the charge applier 56 and charges liquid droplets containing grain P having the predetermined length. The driver 30 then drives the separator 25 and applies a voltage in the predetermined direction between the pair of deflection electrodes. The charged liquid droplet falls while being attracted to one of the two deflection electrodes. As a result, the liquid droplets containing grains P having the predetermined length are separated by one of the deflection electrodes and transferred to and collected by the collector 40.

If the determined from the input data that the grains P do not have the predetermined grain length, the CPU 60 does not generate the drive signals. Therefore, the separator 25 and the charge applier 56 are not driven, and the liquid droplets containing the grains P that do not have the predetermined length are transferred to the reprocessing means 41 without being transferred to the collector 40.

Therefore, the CPU 60 controls the separator 25 and the charge applier 56 based on the data related to the length of the grains P computed by the computation processor 52. Only the grains P having the desired length are separated, and accurate separation of the grains is performed.

The grains P other than those that have the predetermined length and are thus separated by the grain separation means 5 (i.e., grains that are not separated by the grain separation means) are supplied from the grain separation means 5 to the dispersing means 2 by the reprocessing means 41 and reprocessed by the dispersing means 2, the grain orienting means 3, the grain length measuring means 4 and the grain separation means 5.

INDUSTRIAL APPLICABILITY

The present invention is applicable for use in a grain classifying device for classifying grains and an adhesive containing the grains separated by the device.

The invention claimed is:

1. A method for manufacturing an anisotropic conductive adhesive containing a plurality of conductive grains that are needle-shaped, the method comprising:
   dispersing the grains using a disperser;
   orienting the dispersed grains, wherein the orienting includes using a flow passage for orienting each of the dispersed grains in a longitudinal direction of each grain while spacing the grains apart from one another in the longitudinal direction;
   measuring, by a measurer, the length of each of the grains oriented in the longitudinal direction;
   separating, by a separator, grains having a predetermined length from the dispersed grains based on data related to the lengths of the measured grains;
   forming the anisotropic conductive adhesive containing the grains having the predetermined length; and
   supplying to the disperser, by a reprocessor, grains other than the grains having the predetermined length.

* * * * *